United States Patent
Lane et al.

(10) Patent No.: US 8,211,169 B2
(45) Date of Patent: Jul. 3, 2012

(54) GASKET WITH COLLAR FOR PROSTHETIC HEART VALVES AND METHODS FOR USING THEM

(75) Inventors: Ernest Lane, Huntington Beach, CA (US); Michael J. Drews, Sacramento, CA (US); Donnell W. Gurskis, Belmont, CA (US)

(73) Assignee: Medtronic, Inc., Minneapolis, MN (US)

( * ) Notice: Subject to any disclaimer, the term of this patent is extended or adjusted under 35 U.S.C. 154(b) by 1227 days.

(21) Appl. No.: 11/420,720

(22) Filed: May 26, 2006

(65) Prior Publication Data

US 2007/0016285 A1    Jan. 18, 2007

Related U.S. Application Data

(60) Provisional application No. 60/685,265, filed on May 27, 2005, provisional application No. 60/748,640, filed on Dec. 7, 2005.

(51) Int. Cl.
*A61F 2/24* (2006.01)
(52) U.S. Cl. .................. 623/2.1; 623/2.17; 623/2.18
(58) Field of Classification Search ............... 623/1.26, 623/2.14
See application file for complete search history.

(56) References Cited

U.S. PATENT DOCUMENTS

| | | |
|---|---|---|
| 3,143,742 A | 8/1964 | Cromie |
| 3,320,974 A | 5/1967 | High et al. |
| 3,370,305 A | 2/1968 | Goott et al. |
| 3,371,352 A | 3/1968 | Siposs |
| 3,409,013 A | 11/1968 | Berry |
| 3,464,065 A | 9/1969 | Cromie |
| 3,546,710 A | 12/1970 | Ivanovich et al. |
| 3,571,815 A | 3/1971 | Somyk |
| 3,574,865 A | 4/1971 | Hamaker |
| 3,628,535 A | 12/1971 | Ostrowsky et al. |
| 3,686,740 A | 8/1972 | Shiley |
| 3,691,567 A | 9/1972 | Cromie |
| 3,710,744 A | 1/1973 | Goodenough et al. |
| 3,744,060 A | 7/1973 | Bellhouse et al. |
| 3,755,823 A | 9/1973 | Hancock |
| 3,800,403 A | 4/1974 | Anderson et al. |
| 3,839,741 A | 10/1974 | Haller |

(Continued)

FOREIGN PATENT DOCUMENTS

CN         2356656         1/2000

(Continued)

OTHER PUBLICATIONS

Lutter, et al., Percutaneous Valve Replacement: Current State and Future Prospects; Ann. Thorac. Surg. 2004;78:2199-2206.

(Continued)

*Primary Examiner* — Thomas J Sweet
*Assistant Examiner* — Jason-Dennis Stewart

(57) ABSTRACT

A heart valve assembly includes a prosthesis for receiving a prosthetic valve to replace a preexisting natural or prosthetic heart valve within a biological annulus adjacent a sinus cavity. The prosthesis includes an annular member implantable within the biological annulus for contacting tissue surrounding the biological annulus to provide an opening through the biological annulus, a collar extending upwardly from the annular member, and a sewing cuff extending radially outwardly from the annular member and/or collar. Optionally, the annular member and/or collar may be resiliently compressible, expandable, and/or otherwise biased. A valve member, e.g., a mechanical or bioprosthetic valve may be coupled to the collar, e.g., using a drawstring, sutures, or other connectors, to secure the valve member to the gasket member.

14 Claims, 9 Drawing Sheets

U.S. PATENT DOCUMENTS

| | | |
|---|---|---|
| 3,959,827 A | 6/1976 | Kaster |
| 3,974,854 A | 8/1976 | Kurpanek |
| 3,996,623 A | 12/1976 | Kaster |
| 3,997,923 A | 12/1976 | Possis |
| 4,035,849 A | 7/1977 | Angell et al. |
| 4,078,268 A | 3/1978 | Possis |
| 4,078,468 A | 3/1978 | Civitello |
| 4,084,268 A | 4/1978 | Ionexcu et al. |
| 4,106,129 A | 8/1978 | Carpentier et al. |
| 4,164,046 A | 8/1979 | Cooley |
| 4,172,295 A | 10/1979 | Batten |
| 4,211,325 A | 7/1980 | Wright |
| 4,217,665 A | 8/1980 | Bex et al. |
| 4,218,782 A | 8/1980 | Rygg |
| 4,245,358 A | 1/1981 | Moasser |
| 4,259,753 A | 4/1981 | Liotta et al. |
| 4,291,420 A | 9/1981 | Reul |
| 4,297,749 A | 11/1981 | Davis et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,477,930 A | 10/1984 | Totten et al. |
| 4,485,816 A | 12/1984 | Krumme |
| 4,501,030 A | 2/1985 | Lane |
| 4,506,394 A | 3/1985 | Bedard |
| 4,535,483 A | 8/1985 | Klawitter et al. |
| 4,548,202 A | 10/1985 | Duncan |
| 4,605,407 A | 8/1986 | Black et al. |
| 4,626,255 A | 12/1986 | Reichart et al. |
| 4,629,459 A | 12/1986 | Ionescu et al. |
| 4,665,906 A | 5/1987 | Jervis |
| 4,666,442 A | 5/1987 | Arru et al. |
| 4,680,031 A | 7/1987 | Alonso |
| 4,683,883 A | 8/1987 | Martin |
| 4,687,483 A | 8/1987 | Fisher et al. |
| 4,692,164 A | 9/1987 | Dzemeshkievich et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,743,253 A | 5/1988 | Magladry |
| 4,758,151 A | 7/1988 | Arru et al. |
| 4,775,378 A | 10/1988 | Knoch et al. |
| 4,778,461 A | 10/1988 | Pietsch et al. |
| 4,790,843 A | 12/1988 | Carpentier et al. |
| 4,816,029 A | 3/1989 | Penny, III et al. |
| 4,851,000 A | 7/1989 | Gupta |
| 4,865,600 A | 9/1989 | Carpentier et al. |
| 4,888,009 A | 12/1989 | Lederman et al. |
| 4,892,541 A | 1/1990 | Alonso |
| 4,917,097 A | 4/1990 | Proudian et al. |
| 4,917,698 A | 4/1990 | Carpentier et al. |
| 4,935,030 A | 6/1990 | Alonso |
| 4,960,424 A | 10/1990 | Grooters |
| 4,993,428 A | 2/1991 | Arms |
| 4,994,077 A | 2/1991 | Dobben |
| 5,002,567 A | 3/1991 | Bona et al. |
| 5,010,892 A | 4/1991 | Colvin et al. |
| 5,032,128 A | 7/1991 | Alonso |
| 5,035,709 A | 7/1991 | Wieting et al. |
| 5,037,434 A | 8/1991 | Lane |
| 5,071,431 A | 12/1991 | Sauter et al. |
| 5,104,406 A | 4/1992 | Curcio et al. |
| 5,147,391 A | 9/1992 | Lane |
| 5,163,953 A | 11/1992 | Vince |
| 5,163,954 A | 11/1992 | Curcio et al. |
| 5,163,955 A | 11/1992 | Love et al. |
| 5,178,633 A | 1/1993 | Peters |
| 5,192,303 A | 3/1993 | Gatturna et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,370,685 A | 12/1994 | Stevens |
| 5,376,112 A | 12/1994 | Duran |
| 5,396,887 A | 3/1995 | Imran |
| 5,397,346 A | 3/1995 | Walker et al. |
| 5,397,348 A | 3/1995 | Campbell et al. |
| 5,397,351 A | 3/1995 | Pavcnik et al. |
| 5,406,857 A | 4/1995 | Eberhardt et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,531,784 A | 7/1996 | Love et al. |
| 5,533,515 A | 7/1996 | Coller et al. |
| 5,549,665 A | 8/1996 | Vesely et al. |
| 5,549,666 A | 8/1996 | Hata et al. |
| 5,562,729 A | 10/1996 | Purdy et al. |
| 5,571,175 A | 11/1996 | Vanney |
| 5,571,215 A | 11/1996 | Sterman et al. |
| 5,573,007 A | 11/1996 | Bobo, Sr. |
| 5,573,543 A | 11/1996 | Akopov |
| 5,578,076 A | 11/1996 | Krueger et al. |
| 5,584,803 A | 12/1996 | Stevens et al. |
| 5,607,470 A | 3/1997 | Milo |
| 5,613,982 A | 3/1997 | Goldstein |
| 5,618,307 A | 4/1997 | Donlon et al. |
| 5,626,607 A | 5/1997 | Malecki et al. |
| 5,628,789 A | 5/1997 | Vanney et al. |
| 5,662,704 A | 9/1997 | Gross |
| 5,669,917 A | 9/1997 | Sauer |
| 5,693,090 A | 12/1997 | Unsworth et al. |
| 5,695,503 A | 12/1997 | Krueger et al. |
| 5,713,952 A | 2/1998 | Vanney et al. |
| 5,713,953 A | 2/1998 | Vallana et al. |
| 5,716,370 A | 2/1998 | Williamson, IV et al. |
| 5,716,399 A | 2/1998 | Love |
| 5,720,755 A | 2/1998 | Dakov |
| 5,725,554 A | 3/1998 | Simon |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,807,405 A | 9/1998 | Vanney et al. |
| 5,814,097 A | 9/1998 | Sterman et al. |
| 5,814,098 A | 9/1998 | Hinnenkamp et al. |
| 5,814,100 A | 9/1998 | Carpentier et al. |
| 5,824,060 A | 10/1998 | Christie et al. |
| 5,824,061 A | 10/1998 | Quijano et al. |
| 5,824,064 A | 10/1998 | Taheri |
| 5,830,239 A | 11/1998 | Toomes |
| 5,840,081 A | 11/1998 | Andersen et al. |
| 5,843,179 A | 12/1998 | Vanney et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,603 A | 1/1999 | Reif |
| 5,860,992 A | 1/1999 | Daniel |
| 5,861,028 A | 1/1999 | Angell |
| 5,865,801 A | 2/1999 | Houser |
| 5,876,436 A | 3/1999 | Vanney et al. |
| 5,879,371 A | 3/1999 | Gardiner et al. |
| 5,891,160 A | 4/1999 | Williamson, IV et al. |
| 5,891,195 A | 4/1999 | Klostermeyer et al. |
| 5,895,420 A | 4/1999 | Mirsch, II et al. |
| 5,902,308 A | 5/1999 | Murphy |
| 5,908,450 A | 6/1999 | Gross et al. |
| 5,908,452 A | 6/1999 | Bokros et al. |
| 5,910,170 A | 6/1999 | Reimink et al. |

| | | | | | | |
|---|---|---|---|---|---|---|
| 5,919,147 A | 7/1999 | Jain | | 6,402,780 B2 | 6/2002 | Williamson, IV et al. |
| 5,921,934 A | 7/1999 | Teo | | 6,409,759 B1 | 6/2002 | Peredo |
| 5,921,935 A | 7/1999 | Hickey | | 6,413,275 B1 | 7/2002 | Nguyen et al. |
| 5,924,984 A | 7/1999 | Rao | | 6,419,696 B1 | 7/2002 | Ortiz et al. |
| 5,931,969 A | 8/1999 | Carpentier et al. | | 6,425,902 B1 | 7/2002 | Love |
| 5,935,163 A | 8/1999 | Gabbay | | 6,425,916 B1 | 7/2002 | Garrison et al. |
| 5,957,949 A | 9/1999 | Leonhardt et al. | | 6,440,164 B1 | 8/2002 | DiMatteo et al. |
| 5,961,549 A | 10/1999 | Nguyen et al. | | 6,447,524 B1 | 9/2002 | Knodel |
| 5,961,550 A | 10/1999 | Carpentier | | 6,454,799 B1 | 9/2002 | Schreck |
| 5,972,004 A | 10/1999 | Williamson, IV et al. | | 6,458,153 B1 | 10/2002 | Bailey et al. |
| 5,972,024 A | 10/1999 | Northrup, III | | 6,461,382 B1 | 10/2002 | Cao |
| 5,976,183 A | 11/1999 | Ritz | | 6,468,305 B1 | 10/2002 | Otte |
| 5,984,959 A | 11/1999 | Robertson et al. | | 6,503,272 B2 | 1/2003 | Duerig et al. |
| 5,984,973 A | 11/1999 | Girard et al. | | 6,514,265 B2 | 2/2003 | Ho et al. |
| 6,007,577 A | 12/1999 | Vanney et al. | | 6,530,952 B2 | 3/2003 | Vesely |
| 6,010,531 A | 1/2000 | Donlon et al. | | 6,547,827 B2 | 4/2003 | Carpentier et al. |
| 6,042,607 A | 3/2000 | Williamson, IV et al. | | 6,551,332 B1 | 4/2003 | Nguyen et al. |
| 6,045,576 A | 4/2000 | Starr et al. | | 6,558,418 B2 | 5/2003 | Carpentier et al. |
| 6,059,827 A | 5/2000 | Fenton, Jr. | | 6,569,196 B1 | 5/2003 | Vesely |
| 6,066,160 A | 5/2000 | Colvin et al. | | 6,582,462 B1 | 6/2003 | Andersen et al. |
| 6,068,657 A | 5/2000 | Lapeyre et al. | | 6,585,766 B1 | 7/2003 | Huynh et al. |
| 6,074,401 A | 6/2000 | Gardiner et al. | | 6,589,279 B1 | 7/2003 | Anderson et al. |
| 6,074,417 A | 6/2000 | Peredo | | 6,598,307 B2 | 7/2003 | Love et al. |
| 6,074,418 A | 6/2000 | Buchanan et al. | | 6,602,289 B1 | 8/2003 | Colvin et al. |
| 6,081,737 A | 6/2000 | Shah | | 6,607,541 B1 | 8/2003 | Gardiner et al. |
| 6,083,179 A | 7/2000 | Oredsson | | 6,613,059 B2 | 9/2003 | Ho et al. |
| 6,096,074 A | 8/2000 | Pedros | | 6,613,085 B1 | 9/2003 | Anderson et al. |
| 6,099,475 A | 8/2000 | Seward et al. | | 6,641,593 B1 | 11/2003 | Schaller et al. |
| 6,102,944 A | 8/2000 | Huynh | | 6,652,578 B2 | 11/2003 | Bailey et al. |
| 6,106,550 A | 8/2000 | Magovern et al. | | 6,676,671 B1 | 1/2004 | Robertson et al. |
| 6,110,200 A | 8/2000 | Hinnenkamp | | 6,678,962 B1 | 1/2004 | Love et al. |
| 6,113,632 A | 9/2000 | Reif | | 6,682,559 B2 | 1/2004 | Myers et al. |
| 6,117,091 A | 9/2000 | Young et al. | | 6,685,739 B2 | 2/2004 | DiMatteo et al. |
| 6,126,007 A | 10/2000 | Kari et al. | | 6,692,513 B2 | 2/2004 | Streeter et al. |
| 6,129,758 A | 10/2000 | Love | | 6,695,859 B1 | 2/2004 | Golden et al. |
| 6,139,575 A | 10/2000 | Shu et al. | | 6,709,457 B1 | 3/2004 | Otte et al. |
| 6,143,024 A | 11/2000 | Campbell et al. | | 6,716,243 B1 | 4/2004 | Colvin et al. |
| 6,143,025 A | 11/2000 | Stobie et al. | | 6,716,244 B2 | 4/2004 | Klaco |
| 6,149,658 A | 11/2000 | Gardiner et al. | | 6,719,789 B2 | 4/2004 | Cox |
| 6,162,233 A | 12/2000 | Williamson, IV et al. | | 6,719,790 B2 | 4/2004 | Brendzel et al. |
| 6,165,183 A | 12/2000 | Kuehn et al. | | 6,730,118 B2 | 5/2004 | Spenser et al. |
| 6,168,614 B1 | 1/2001 | Anderson et al. | | 6,733,525 B2 | 5/2004 | Yang |
| 6,176,877 B1 | 1/2001 | Buchanan et al. | | 6,764,508 B1 | 7/2004 | Roehe et al. |
| 6,183,512 B1 | 2/2001 | Howanec, Jr. et al. | | 6,767,362 B2 | 7/2004 | Schreck |
| 6,197,054 B1 | 3/2001 | Hamblin, Jr. et al. | | 6,769,434 B2 | 8/2004 | Liddicoat et al. |
| 6,200,306 B1 | 3/2001 | Klostermeyer | | 6,776,785 B1 | 8/2004 | Yencho |
| 6,203,553 B1 | 3/2001 | Robertson | | 6,786,924 B2 | 9/2004 | Ryan et al. |
| 6,214,043 B1 | 4/2001 | Krueger et al. | | 6,786,925 B1 | 9/2004 | Schoon et al. |
| 6,217,610 B1 | 4/2001 | Carpentier et al. | | 6,790,229 B1 | 9/2004 | Berreklouw |
| 6,217,611 B1 | 4/2001 | Klostermeyer | | 6,790,230 B2 | 9/2004 | Beyersdorf et al. |
| 6,231,561 B1 | 5/2001 | Frazier et al. | | 6,805,711 B2 | 10/2004 | Quijano et al. |
| 6,231,602 B1 | 5/2001 | Carpentier et al. | | 6,830,585 B1 | 12/2004 | Artof et al. |
| 6,241,765 B1 | 6/2001 | Griffin et al. | | 6,833,924 B2 | 12/2004 | Love et al. |
| 6,245,102 B1 | 6/2001 | Jayaraman | | 6,837,902 B2 | 1/2005 | Nguyen et al. |
| 6,245,105 B1 | 6/2001 | Nguyen et al. | | 6,846,324 B2 | 1/2005 | Stobie |
| 6,254,636 B1 | 7/2001 | Peredo | | 6,846,325 B2 | 1/2005 | Liddicoat |
| 6,264,691 B1 | 7/2001 | Gabbay | | 6,872,226 B2 | 3/2005 | Cali et al. |
| 6,270,526 B1 | 8/2001 | Cox | | 6,893,459 B1 | 5/2005 | Macoviak |
| 6,270,527 B1 | 8/2001 | Campbell et al. | | 6,893,460 B2 | 5/2005 | Spenser et al. |
| 6,283,127 B1 | 9/2001 | Sterman et al. | | 6,896,690 B1 | 5/2005 | Lambrecht et al. |
| 6,283,995 B1 | 9/2001 | Moe et al. | | 6,908,481 B2 | 6/2005 | Cribier |
| 6,287,339 B1 | 9/2001 | Vazquez et al. | | 6,911,043 B2 | 6/2005 | Myers et al. |
| 6,290,674 B1 | 9/2001 | Roue et al. | | 6,913,607 B2 | 7/2005 | Ainsworth et al. |
| 6,299,638 B1 | 10/2001 | Sauter | | 6,918,917 B1 | 7/2005 | Nguyen et al. |
| 6,309,417 B1 | 10/2001 | Spence | | 6,921,407 B2 | 7/2005 | Nguyen et al. |
| 6,312,447 B1 | 11/2001 | Grimes | | 6,926,730 B1 | 8/2005 | Nguyen et al. |
| 6,312,465 B1 | 11/2001 | Griffin et al. | | 6,929,653 B2 | 8/2005 | Streeter |
| 6,319,280 B1 | 11/2001 | Schoon | | 6,939,365 B1 | 9/2005 | Fogarty |
| 6,319,281 B1 | 11/2001 | Patel | | 6,945,980 B2 | 9/2005 | Nguyen et al. |
| 6,322,588 B1 | 11/2001 | Ogle et al. | | 6,945,997 B2 | 9/2005 | Huynh et al. |
| 6,328,727 B1 | 12/2001 | Frazier et al. | | 6,960,221 B2 | 11/2005 | Ho et al. |
| 6,328,763 B1 | 12/2001 | Love et al. | | 6,974,476 B2 | 12/2005 | McGuckin et al. |
| 6,338,740 B1 | 1/2002 | Carpentier | | 7,011,681 B2 | 3/2006 | Vesely |
| 6,350,281 B1 | 2/2002 | Rhee | | 7,025,780 B2 | 4/2006 | Gabbay |
| 6,358,278 B1 | 3/2002 | Brendzel et al. | | 7,037,333 B2 | 5/2006 | Myers et al. |
| 6,358,556 B1 | 3/2002 | Ding et al. | | 7,070,616 B2 | 7/2006 | Majercak et al. |
| 6,371,983 B1 | 4/2002 | Lane | | 7,083,648 B2 | 8/2006 | Yu |
| 6,391,053 B1 | 5/2002 | Brendzel et al. | | 7,097,659 B2 | 8/2006 | Woolfson et al. |
| 6,395,025 B1 | 5/2002 | Fordenbacher et al. | | 7,101,396 B2 | 9/2006 | Artof et al. |

| Patent/Pub No. | Date | Name |
|---|---|---|
| 7,137,184 B2 | 11/2006 | Schreck |
| 7,141,064 B2 | 11/2006 | Scott et al. |
| 7,147,663 B1 | 12/2006 | Berg et al. |
| 7,153,324 B2 | 12/2006 | Case et al. |
| 7,172,625 B2 | 2/2007 | Shu et al. |
| 7,175,659 B2 | 2/2007 | Hill et al. |
| 7,182,769 B2 | 2/2007 | Ainsworth et al. |
| 7,186,265 B2 | 3/2007 | Sharkawy et al. |
| 7,195,641 B2 | 3/2007 | Palmaz et al. |
| 7,201,761 B2 | 4/2007 | Woolfson et al. |
| 7,201,771 B2 | 4/2007 | Lane |
| 7,201,772 B2 | 4/2007 | Schwammenthal et al. |
| 7,214,344 B2 | 5/2007 | Carpentier et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| RE40,377 E | 6/2008 | Williamson, IV et al. |
| 7,393,360 B2 | 7/2008 | Spenser et al. |
| 7,422,603 B2 | 9/2008 | Lane |
| 7,445,632 B2 | 11/2008 | McGuckin et al. |
| 7,513,909 B2 | 4/2009 | Lane et al. |
| 7,547,313 B2 | 6/2009 | Gardiner et al. |
| 7,556,647 B2 | 7/2009 | Drews et al. |
| 7,578,843 B2 | 8/2009 | Shu |
| 7,597,711 B2 | 10/2009 | Drews et al. |
| 7,708,775 B2 | 5/2010 | Rowe et al. |
| 7,722,643 B2 | 5/2010 | Ho et al. |
| 7,744,611 B2 | 6/2010 | Nguyen et al. |
| 7,763,040 B2 | 7/2010 | Schaller et al. |
| 7,771,469 B2 | 8/2010 | Liddicoat |
| 7,803,184 B2 | 9/2010 | McGuckin et al. |
| 2001/0007956 A1 | 7/2001 | Letac et al. |
| 2001/0018592 A1 | 8/2001 | Schaller et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1* | 2/2002 | Lane et al. ............ 623/2.14 |
| 2002/0032481 A1 | 3/2002 | Gabbay |
| 2002/0055774 A1 | 5/2002 | Liddicoat |
| 2002/0058994 A1 | 5/2002 | Hill et al. |
| 2002/0058995 A1 | 5/2002 | Stevens |
| 2002/0077555 A1 | 6/2002 | Schwartz |
| 2002/0077698 A1 | 6/2002 | Peredo |
| 2002/0091441 A1 | 7/2002 | Guzik |
| 2002/0116054 A1 | 8/2002 | Lundell et al. |
| 2002/0123802 A1 | 9/2002 | Snyders |
| 2002/0128684 A1 | 9/2002 | Foerster |
| 2002/0138138 A1 | 9/2002 | Yang |
| 2002/0151970 A1 | 10/2002 | Garrison et al. |
| 2002/0173842 A1 | 11/2002 | Buchanan |
| 2002/0177223 A1 | 11/2002 | Ogle et al. |
| 2002/0183834 A1 | 12/2002 | Klaco |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023302 A1 | 1/2003 | Moe et al. |
| 2003/0023303 A1 | 1/2003 | Palmaz et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0045902 A1 | 3/2003 | Weadeock |
| 2003/0055495 A1 | 3/2003 | Pease et al. |
| 2003/0109922 A1 | 6/2003 | Peterson |
| 2003/0109924 A1 | 6/2003 | Cribier |
| 2003/0114913 A1 | 6/2003 | Spenser et al. |
| 2003/0125793 A1 | 7/2003 | Vesely |
| 2003/0130729 A1 | 7/2003 | Paniagua et al. |
| 2003/0149477 A1 | 8/2003 | Gabbay |
| 2003/0149478 A1 | 8/2003 | Figulla et al. |
| 2003/0153974 A1 | 8/2003 | Spenser et al. |
| 2003/0167089 A1 | 9/2003 | Lane |
| 2003/0191481 A1 | 10/2003 | Nguyen et al. |
| 2003/0199963 A1 | 10/2003 | Tower et al. |
| 2003/0199971 A1 | 10/2003 | Tower et al. |
| 2003/0229394 A1 | 12/2003 | Ogle et al. |
| 2003/0236568 A1 | 12/2003 | Hojeibane et al. |
| 2004/0015232 A1 | 1/2004 | Shu |
| 2004/0019374 A1 | 1/2004 | Hojeibane et al. |
| 2004/0024452 A1 | 2/2004 | Kruse et al. |
| 2004/0030381 A1* | 2/2004 | Shu .................. 623/2.11 |
| 2004/0034411 A1 | 2/2004 | Quijano et al. |
| 2004/0039436 A1 | 2/2004 | Spenser et al. |
| 2004/0044406 A1 | 3/2004 | Woolfson |
| 2004/0050393 A1 | 3/2004 | Golden et al. |
| 2004/0068276 A1 | 4/2004 | Golden et al. |
| 2004/0078074 A1 | 4/2004 | Anderson et al. |
| 2004/0093075 A1 | 5/2004 | Kuehne |
| 2004/0102797 A1 | 5/2004 | Golden et al. |
| 2004/0106976 A1 | 6/2004 | Bailey et al. |
| 2004/0106990 A1 | 6/2004 | Spence et al. |
| 2004/0122514 A1 | 6/2004 | Fogarty |
| 2004/0122516 A1* | 6/2004 | Fogarty et al. ............ 623/2.37 |
| 2004/0122526 A1 | 6/2004 | Imran |
| 2004/0167573 A1 | 8/2004 | Williamson, IV et al. |
| 2004/0167620 A1 | 8/2004 | Ortiz et al. |
| 2004/0176839 A1 | 9/2004 | Huynh et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0199176 A1 | 10/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu |
| 2004/0210307 A1 | 10/2004 | Khairkhahan |
| 2004/0225355 A1 | 11/2004 | Stevens |
| 2004/0225356 A1 | 11/2004 | Frater |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065601 A1 | 3/2005 | Lee et al. |
| 2005/0065614 A1 | 3/2005 | Stinson |
| 2005/0070924 A1 | 3/2005 | Schaller et al. |
| 2005/0075584 A1 | 4/2005 | Cali |
| 2005/0075659 A1 | 4/2005 | Realyvasquez et al. |
| 2005/0075667 A1 | 4/2005 | Ho et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075730 A1 | 4/2005 | Myers et al. |
| 2005/0080454 A1 | 4/2005 | Drews |
| 2005/0096738 A1 | 5/2005 | Cali et al. |
| 2005/0098547 A1 | 5/2005 | Cali et al. |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137702 A1 | 6/2005 | Haug et al. |
| 2005/0150775 A1 | 7/2005 | Zhang et al. |
| 2005/0159811 A1 | 7/2005 | Lane |
| 2005/0165477 A1 | 7/2005 | Andruiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |

| | | | | | | |
|---|---|---|---|---|---|---|
| 2005/0192665 A1 | 9/2005 | Spenser et al. | | 2007/0225801 A1 | 9/2007 | Drews et al. |
| 2005/0203616 A1 | 9/2005 | Cribier | | 2007/0233237 A1 | 10/2007 | Krivoruchko |
| 2005/0203617 A1 | 9/2005 | Forster et al. | | 2007/0239266 A1 | 10/2007 | Birdsall |
| 2005/0203618 A1 | 9/2005 | Sharkaway et al. | | 2007/0239269 A1 | 10/2007 | Dolan et al. |
| 2005/0216079 A1 | 9/2005 | MaCoviak | | 2007/0239273 A1 | 10/2007 | Allen |
| 2005/0222674 A1 | 10/2005 | Paine | | 2007/0255398 A1 | 11/2007 | Yang et al. |
| 2005/0234546 A1 | 10/2005 | Nugent et al. | | 2007/0260305 A1 | 11/2007 | Drews et al. |
| 2005/0240259 A1 | 10/2005 | Sisken et al. | | 2007/0265701 A1 | 11/2007 | Gurskis et al. |
| 2005/0240263 A1 | 10/2005 | Fogarty | | 2007/0270944 A1 | 11/2007 | Bergheim et al. |
| 2005/0251252 A1 | 11/2005 | Stobie | | 2007/0288089 A1 | 12/2007 | Gurskis et al. |
| 2005/0261765 A1 | 11/2005 | Liddicoat | | 2008/0004696 A1 | 1/2008 | Vesely |
| 2005/0283231 A1 | 12/2005 | Haug et al. | | 2008/0033543 A1 | 2/2008 | Gurskis et al. |
| 2006/0004389 A1 | 1/2006 | Nguyen et al. | | 2008/0071361 A1 | 3/2008 | Tuval et al. |
| 2006/0025857 A1 | 2/2006 | Bergheim et al. | | 2008/0071369 A1 | 3/2008 | Tuval et al. |
| 2006/0052867 A1 | 3/2006 | Revuelta et al. | | 2008/0097595 A1 | 4/2008 | Gabbay |
| 2006/0058871 A1 | 3/2006 | Zakay et al. | | 2008/0119875 A1 | 5/2008 | Ino et al. |
| 2006/0058872 A1 | 3/2006 | Salahieh et al. | | 2008/0281411 A1 | 11/2008 | Berreklouw |
| 2006/0074484 A1 | 4/2006 | Huber | | 2008/0319543 A1 | 12/2008 | Lane |
| 2006/0085060 A1 | 4/2006 | Campbell | | 2009/0036903 A1 | 2/2009 | Ino et al. |
| 2006/0095125 A1 | 5/2006 | Chinn et al. | | 2009/0112233 A1 | 4/2009 | Xiao |
| 2006/0122634 A1 | 6/2006 | Ino | | 2009/0192599 A1 | 7/2009 | Lane et al. |
| 2006/0122692 A1 | 6/2006 | Gilad et al. | | 2009/0192602 A1 | 7/2009 | Kuehn |
| 2006/0135964 A1 | 6/2006 | Vesely | | 2009/0192603 A1 | 7/2009 | Ryan |
| 2006/0136052 A1 | 6/2006 | Vesely | | 2009/0192604 A1 | 7/2009 | Gloss |
| 2006/0136054 A1 | 6/2006 | Berg et al. | | 2009/0192605 A1 | 7/2009 | Gloss et al. |
| 2006/0149360 A1 | 7/2006 | Schwammenthal et al. | | 2009/0192606 A1 | 7/2009 | Gloss et al. |
| 2006/0149367 A1 | 7/2006 | Sieracki | | 2009/0210052 A1 | 8/2009 | Forster et al. |
| 2006/0154230 A1 | 7/2006 | Cunanan | | 2009/0264903 A1 | 10/2009 | Lee et al. |
| 2006/0161249 A1 | 7/2006 | Realyvasquez et al. | | 2009/0319038 A1 | 12/2009 | Gurskis et al. |
| 2006/0167543 A1 | 7/2006 | Bailey et al. | | 2010/0030244 A1 | 2/2010 | Woolfson et al. |
| 2006/0195183 A1 | 8/2006 | Navia et al. | | 2010/0044410 A1 | 2/2010 | Argentine et al. |
| 2006/0195184 A1 | 8/2006 | Lane | | 2010/0100174 A1 | 4/2010 | Gurskis |
| 2006/0195185 A1 | 8/2006 | Lane | | 2010/0249894 A1 | 9/2010 | Oba et al. |
| 2006/0195186 A1 | 8/2006 | Drews | | | | |
| 2006/0207031 A1 | 9/2006 | Cunanan et al. | | FOREIGN PATENT DOCUMENTS | | |
| 2006/0229708 A1 | 10/2006 | Powell et al. | | | | |
| 2006/0235508 A1 | 10/2006 | Lane | | DE | 19532973 | 11/1996 |
| 2006/0241745 A1 | 10/2006 | Solem | | EP | 0 084 395 | 8/1986 |
| 2006/0246888 A1 | 11/2006 | Bender et al. | | EP | 0 096 721 | 12/1987 |
| 2006/0253191 A1 | 11/2006 | Salahieh et al. | | EP | 0 125 393 | 12/1987 |
| 2006/0259134 A1 | 11/2006 | Schwammenthal et al. | | EP | 0 179 562 | 7/1989 |
| 2006/0259135 A1 | 11/2006 | Navia et al. | | EP | 1057460 | 12/2000 |
| 2006/0259136 A1 | 11/2006 | Nguyen et al. | | EP | 1 088 529 | 4/2001 |
| 2006/0265056 A1 | 11/2006 | Nguyen et al. | | EP | 1171059 | 1/2002 |
| 2006/0271172 A1 | 11/2006 | Tehrani | | EP | 971 650 | 1/2005 |
| 2006/0271175 A1 | 11/2006 | Woofson et al. | | EP | 171 059 | 2/2005 |
| 2006/0276888 A1 | 12/2006 | Lee | | GB | 1093599 | 12/1967 |
| 2006/0287717 A1 | 12/2006 | Rowe et al. | | GB | 1477643 | 6/1977 |
| 2006/0287719 A1 | 12/2006 | Rowe et al. | | GB | 2011259 | 7/1979 |
| 2007/0005129 A1 | 1/2007 | Damm et al. | | GB | 2 056 023 | 3/1981 |
| 2007/0010835 A1 | 1/2007 | Breton et al. | | GB | 2 069 843 | 9/1981 |
| 2007/0010876 A1 | 1/2007 | Salahieh et al. | | GB | 2254254 | 10/1992 |
| 2007/0010877 A1 | 1/2007 | Salahieh et al. | | GB | 2 279 134 | 12/1994 |
| 2007/0016285 A1 | 1/2007 | Lane | | SU | 1116573 | 7/1985 |
| 2007/0016286 A1 | 1/2007 | Herrmann et al. | | WO | 87/05489 | 9/1987 |
| 2007/0016288 A1 | 1/2007 | Gurskis | | WO | 89/00084 | 2/1989 |
| 2007/0027461 A1 | 2/2007 | Gardiner et al. | | WO | 91/15167 | 10/1991 |
| 2007/0043435 A1 | 2/2007 | Seguin et al. | | WO | 92/01269 | 8/1992 |
| 2007/0078509 A1 | 4/2007 | Lotfy | | WO | 92/13502 | 8/1992 |
| 2007/0078510 A1 | 4/2007 | Ryan | | WO | 92/19184 | 11/1992 |
| 2007/0095698 A1 | 5/2007 | Cambron | | WO | 92/19185 | 11/1992 |
| 2007/0100440 A1 | 5/2007 | Figulla et al. | | WO | 95/17139 | 6/1995 |
| 2007/0106313 A1 | 5/2007 | Golden et al. | | WO | 95/28899 | 11/1995 |
| 2007/0129794 A1 | 6/2007 | Realyvasquez | | WO | 96/40006 | 12/1996 |
| 2007/0142848 A1 | 6/2007 | Ainsworth et al. | | WO | 97/09933 | 3/1997 |
| 2007/0142906 A1 | 6/2007 | Figulla et al. | | WO | 97/09944 | 3/1997 |
| 2007/0142907 A1 | 6/2007 | Moaddeb et al. | | WO | 97/27799 | 8/1997 |
| 2007/0150053 A1 | 6/2007 | Gurskis | | WO | 97/41801 | 11/1997 |
| 2007/0156233 A1 | 7/2007 | Kapadia et al. | | WO | 97/42871 | 11/1997 |
| 2007/0162103 A1 | 7/2007 | Case et al. | | WO | 98/06329 | 2/1998 |
| 2007/0162107 A1 | 7/2007 | Haug et al. | | WO | 99/11201 | 3/1999 |
| 2007/0162111 A1 | 7/2007 | Fukamachi et al. | | WO | 99/15112 | 4/1999 |
| 2007/0162113 A1 | 7/2007 | Sharkawy et al. | | WO | 99/51169 | 10/1999 |
| 2007/0179604 A1 | 8/2007 | Lane | | WO | 00/32105 | 6/2000 |
| 2007/0185565 A1 | 8/2007 | Schwammenthal et al. | | WO | 00/40176 | 7/2000 |
| 2007/0198097 A1 | 8/2007 | Zegdi | | WO | 00/44311 | 8/2000 |
| 2007/0203575 A1 | 8/2007 | Forster et al. | | WO | 00/56250 | 9/2000 |
| 2007/0203576 A1 | 8/2007 | Lee et al. | | WO | 00/59382 | 10/2000 |
| 2007/0213813 A1 | 9/2007 | Von Segesser et al. | | WO | 00/60995 | 10/2000 |
| | | | | WO | 00/64380 | 11/2000 |

| | | |
|---|---|---|
| WO | 01/10310 | 2/2001 |
| WO | 01/10312 | 2/2001 |
| WO | 01/49217 | 7/2001 |
| WO | 01/58363 | 8/2001 |
| WO | 01/76510 | 10/2001 |
| WO | 01/82840 | 11/2001 |
| WO | 01/87190 | 11/2001 |
| WO | 03/063740 | 8/2003 |
| WO | 2004/006810 | 1/2004 |
| WO | 2004/089246 | 10/2004 |
| WO | 2005/004753 | 1/2005 |
| WO | 2005/020842 | 3/2005 |
| WO | 2005/039452 | 5/2005 |
| WO | 2005/072655 | 8/2005 |
| WO | 2006/086135 | 8/2006 |
| WO | 2009/137517 | 11/2009 |

OTHER PUBLICATIONS

Jansen, et al., "Detachable Shape-Memory Sewing Ring for Heart Valves," Artif. Organs. vol. 16, No. 3, 1992, pp. 294-297, Helmholtz Institute for Biomedical Engineering, Technical University of Aachen, Aachn, Germany.

* cited by examiner

*Section A-A*

*Section B-B*

GASKET WITH COLLAR FOR PROSTHETIC HEART VALVES AND METHODS FOR USING THEM

RELATED APPLICATION DATA

This application claims benefit of provisional application Ser. Nos. 60/685,265, filed May 27, 2005 and 60/748,640, field Dec. 7, 2005, the entire disclosures of which are expressly incorporated herein by reference.

FIELD OF THE INVENTON

The present invention relates generally to heart valves that may be implanted within a patient, and, more particularly, to multiple component heart valve assemblies that may be assembled together, and to apparatus and methods for using them.

BACKGROUND

Prosthetic heart valves can replace defective human valves in patients. For example, one piece valves have been suggested that include sewing rings or suture cuffs that are attached to and extend around the outer circumference of a prosthetic valve. In addition, multiple component valves have also been suggested that include a sewing ring that is separate from a valve component. The sewing rings of either type of prosthetic valve can be tedious and time consuming to secure within a target site, i.e., within an annulus of a heart where a natural heart valve has been removed.

For example, to implant a sewing ring within an annulus of a heart, between twelve and twenty sutures may be secured initially to tissue surrounding the annulus. The sewing ring and/or the entire prosthetic valve may then be advanced or "parachuted" down the sutures into the annulus. Knots may then be tied with the sutures to secure the sewing ring within the annulus, whereupon the sutures may be cut. Consequently, this procedure can be very complicated, requiring management and manipulation of many sutures. The complexity of the procedure also provides a greater opportunity for mistakes and requires a patient to be on cardiopulmonary bypass for a lengthy period of time.

Because the annulus of the heart may not match the circular cross-section of the sewing ring and/or prosthetic valve, the prosthetic valve may not fit optimally within the annulus. As a result, natural blood hemodynamics through and around the valve may be impaired, resulting in clotting, possible emboli production, and eventual calcification of the valve structure.

To address this concern, flexible sewing rings have been suggested for use with multiple component valves. The sewing ring may be implanted within the annulus, e.g., using the procedure described above, i.e., parachuted down an arrangement of sutures. The sewing ring may conform at least partially to the anatomy of the annulus. Alternatively, instead of using sutures, it has also been suggested to drive staples through the sewing ring into the surrounding tissue to secure the sewing ring.

When a mechanical or prosthetic valve is then attached to the sewing ring, however, the valve and sewing ring may not mate together effectively, e.g., if the shape of the sewing ring has been distorted to conform to the annulus, which may also impair natural blood hemodynamics, create leaks, and/or otherwise impair performance of the prosthetic valve.

SUMMARY OF THE INVENTION

The present invention is directed to heart valves that may be implanted within a patient, and, more particularly, to multiple component heart valve assemblies that may be assembled together, and to apparatus and methods for making and implanting them.

In accordance with one embodiment, a prosthesis is provided for receiving a prosthetic valve to replace a preexisting natural or prosthetic heart valve within a biological annulus adjacent a sinus cavity. The prosthesis may include an annular member implantable within the biological annulus for contacting tissue surrounding the biological annulus to provide an opening through the biological annulus, a collar extending upwardly from the annular member, and a sewing cuff extending radially outwardly from the annular member and/or collar. Optionally, the annular member and/or collar may be resiliently compressible, expandable, and/or otherwise biased.

In accordance with another embodiment, a heart valve assembly is provided for implantation within a biological annulus. The heart valve assembly may include an annular prosthesis implantable within a biological annulus that includes an annular member for contacting tissue surrounding the biological annulus, and a collar extending upwardly from the annular member. The heart valve assembly also includes a prosthetic valve, e.g., including a mechanical or bioprosthetic heart valve, which may have a circular or multiple lobular shape for implantation above the biological annulus.

Optionally, one or more connectors may be provided on at least one of the annular prosthesis and the prosthetic valve for securing the prosthetic valve to the annular prosthesis. For example, the one or more connectors may include a drawstring on the collar for engaging a frame of the prosthetic valve. Alternatively, the one or more connectors may include one or more latches, detents, interlocking elements on the prosthetic valve and/or the annular prosthesis.

In one embodiment, the collar may be formed from resiliently flexible material, e.g., silicone covered with a fabric covering. The collar may be formed as a unitary piece with a sewing ring and/or annular member, which may be covered with one or more pieces of fabric. Alternatively, the collar, sewing ring, and/or annular member may be separate components that are attached to one another, either before or after being covered with fabric.

In accordance with yet another embodiment, a method is provided for implanting a prosthetic heart valve assembly to replace a natural or prosthetic heart valve implanted within a biological annulus below a sinus cavity. An annular member may be introduced into the biological annulus, e.g., to direct tissue surrounding the biological annulus outwardly, e.g., to at least partially dilate the biological annulus. A flexible sewing cuff or skirt may extend around the annular member that may receive one or more connectors, e.g., sutures, clips, and the like, to secure the annular member within the annulus.

A valve prosthesis, e.g., a mechanical or bioprosthetic valve, may be advanced into the sinus cavity, and secured relative to the annular member. In one embodiment, a collar or stand-off extends upwardly from the annular member for receiving the valve prosthesis. The valve prosthesis may be secured to the collar using one or more connectors, e.g., a drawstring in the collar, one or more sutures, clips detents, and/or other cooperating connectors, e.g., on the collar and a frame of the valve prosthesis.

The collar may support the valve prosthesis above the tissue annulus, e.g., within the sinus of valsalva. The collar may allow the valve prosthesis to have a larger size than the annular member, thereby enhancing the fluid flow or other performance characteristics of the implanted heart valve assembly. Optionally, the collar may include a funnel or other tapered shape that may provide a transition from a relatively larger valve prosthesis to the annular member within the tissue annulus. In addition, the collar may support the valve prosthesis away from a wall of the sinus or other supra-annular space, while still allowing blood to flow easily into the coronary arteries around the valve prosthesis.

In accordance with still another embodiment, a heart valve prosthesis is provided that includes an annular prosthesis implantable within a biological annulus, and a prosthetic valve member secured to the annular prosthesis. The annulus prosthesis may include an annular member sized for implantation within the biological annulus, a sewing cuff extending radially from the annular member, and an annular transition extending upwardly from the annular member. The valve member may include a frame secured to the annular transition, the frame having a cross-section that is substantially larger than the annular member.

In accordance with yet another embodiment, a method is provided for implanting a prosthetic heart valve assembly within a biological annulus. The heart valve assembly includes an annular member sized for delivery into the biological annulus, an annular transition extending upwardly from the annular ring, and a valve member secured to the annular transition that has a cross-section larger than the annular member. The heart valve assembly may be introduced towards the biological annulus such that the annular member is disposed within the biological annulus and the valve member is disposed above the biological annulus, and the heart valve assembly may be secured to tissue adjacent the biological annulus.

In one embodiment, a valve member is selected having a predetermined size corresponding to a sinus cavity above the biological annulus, and the selected valve member is secured to the annular transition before introduction into the biological annulus. In another embodiment, the valve member is secured to the annular transition during manufacturing and provided preassembled. In still another embodiment, the annular transition may be implanted within the biological annulus, and then the valve member may be introduced and secured to the annular transition.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE PREFERRED EMBODIMENTS

Figure 1:
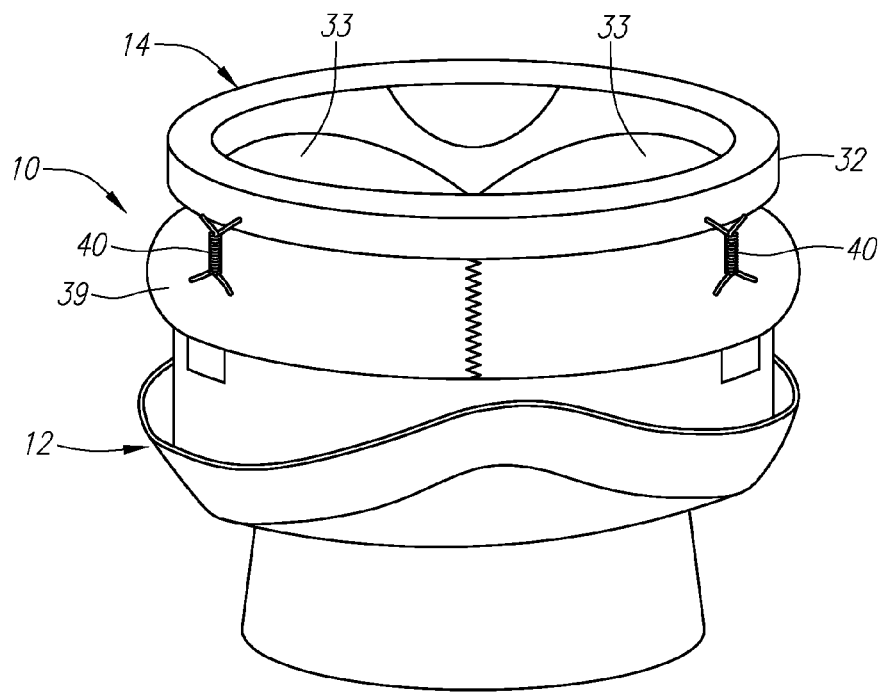
FIG. 1 is a perspective view of a two piece heart valve assembly including a gasket member and a mechanical valve.
Figure 2:
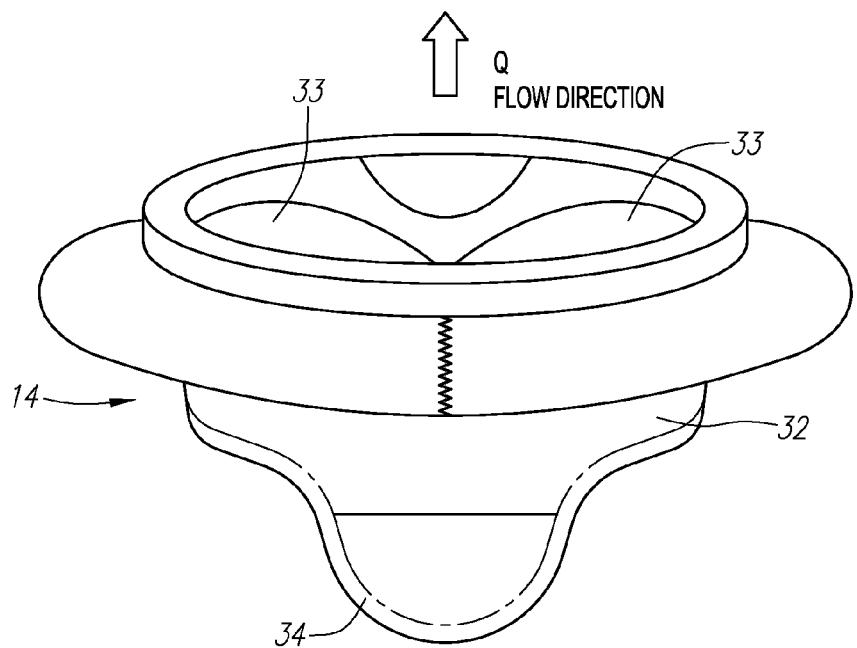
FIG. 2 is a perspective view of an exemplary mechanical valve that may be provided with the heart valve assembly of FIG. 1.
Figure 4A:
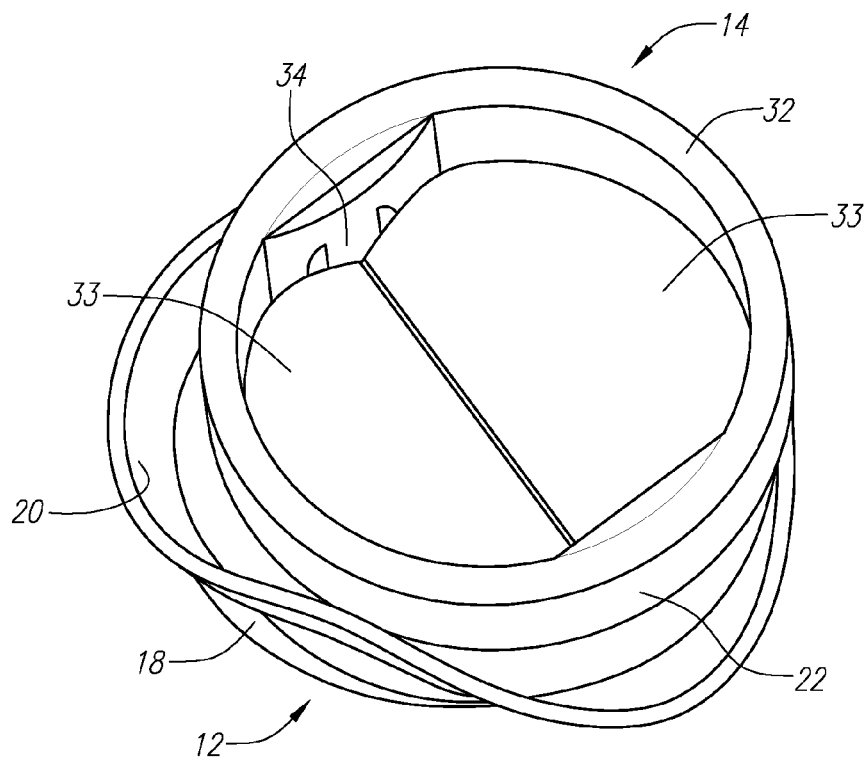
FIGS. 4A and 4B are perspective and partial cross-sectional side views, respectively, of the heart valve assembly of FIG. 1.

Turning to the drawings, FIG. 1 shows an exemplary embodiment of a heart valve assembly 10 that generally includes a gasket member 12 and a valve member 14. As shown, the valve member 14 may be a mechanical valve including an annular frame 32 supporting a pair of valve members 33 that open and close within the frame 32 (e.g., see FIGS. 5 and 4A, respectively). Optionally, as best seen in FIG. 2, the valve member 14 may include a pair of ears 34 extending downwardly from the frame 32, e.g., for pivotally securing the valve members 33 to the frame 32.

In an exemplary embodiment, the valve member 14 may be a mechanical valve, such as the "Regent" Bileaflet Valve manufactured by St. Jude Medical. In alternative embodiments, the valve member 14 may be other mechanical or bioprosthetic valves, such as those disclosed in co-pending application Ser. No. 10/646,63, filed Aug. 22, 2003, Ser. No. 10/681,700, filed Oct. 8, 2003, Ser. No. 10/765,725, filed Jan. 26, 2004, Ser. No. 11/069,081, filed Feb. 28, 2005, and 60/669,704, filed Apr. 8, 2005. The entire disclosures of these applications are expressly incorporated by reference herein.

Turning to FIGS. 3A-3D, an exemplary embodiment of the gasket member 12 is shown that generally includes an annular ring 18, a sewing cuff 20, and a collar or stand-off 22. A fabric covering, which may be provided on one or more components of the gasket member 12 has been omitted for clarity. In one embodiment, the annular ring 18 may have a generally circular shape, although alternatively, the annular ring 18 may have a multi-lobular shape about the circumference, e.g., including three lobes separated by scallops or cusps (not shown). Optionally, the annular ring 18 may be expandable and/or contractible such that the diameter may be adjusted, e.g., based upon the anatomy of the patient encountered during a procedure. In one embodiment, the annular ring 18 may be biased to expand to a predetermined diameter. Thus, the annular ring 18 may be contracted radially to a smaller diameter, e.g., to facilitate delivery into an annulus, yet may be resiliently expandable to dilate tissue surrounding the annulus and/or to facilitate securing the gasket member 12 within the annulus. In addition, if the sewing cuff 20 and/or collar 22 are substantially flexible, they may also be at least partially folded or otherwise compressed to facilitate introduction into a biological annulus.

Figure 4B:
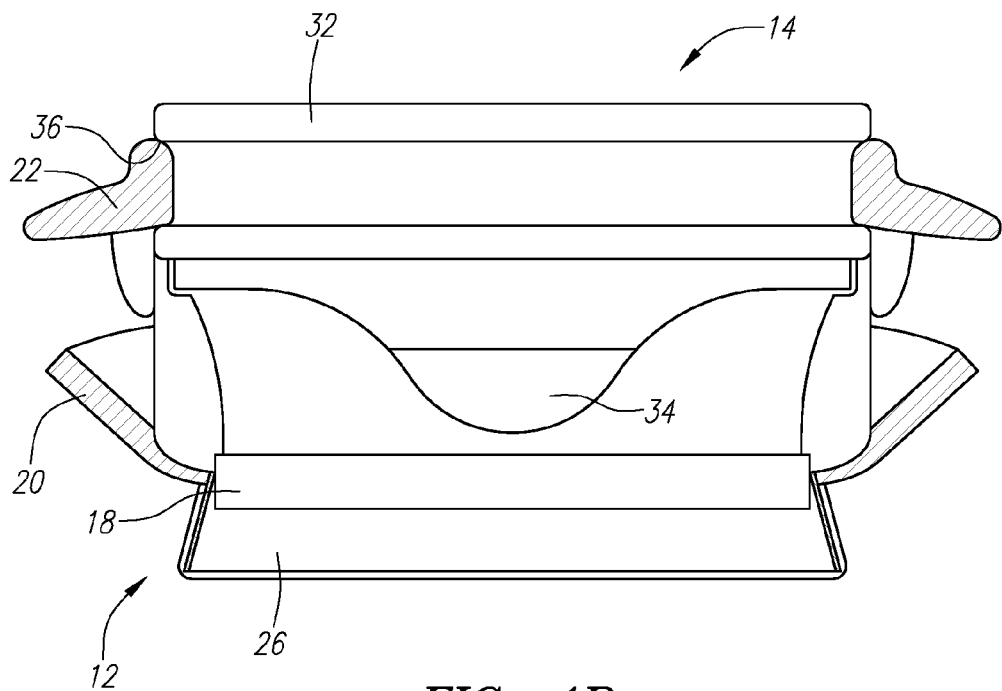

With additional reference to FIG. 4B, the annular ring 18 may be formed from an elastic or superelastic material, such as Nitinol, or any of the other materials described in the applications incorporated by reference herein. For example, the annular ring 18 may be cut from a flat sheet of base material having a desired thickness for the annular ring 18, for example, by laser cutting, mechanical cutting, and the like. Thus, the annular ring 18 may be initially formed as a long band of material, having a width corresponding to the desired width of the annular ring 18. The band may be wrapped around a mandrel or otherwise restrained in a generally cylindrical shape with the ends adjacent to one another, and the band may be heat treated or otherwise processed to program the generally cylindrical shape to create the annular ring 218. The generally cylindrical shape may include the ends overlapping one another, spaced apart from one another to provide an open "C" shape, or attached to one another.

When the annular ring 18 is at least partially covered with fabric, as shown in FIG. 1, e.g., for tissue ingrowth, the fabric may be wrapped around the annular ring 18, while accommodating expansion and contraction of the annular ring 18. For example, at least near the ends (not shown) of the annular ring 18, the fabric may not be secured to the annular ring 18, allowing the ends to slide circumferentially relative to the fabric. Optionally, sutures and the like (not shown) may be used to secure the fabric to the annular ring 18 at locations removed from the ends, e.g., at an intermediate location about the circumference of the annular ring 18. Alternatively, the entire annular ring 18 may be free to slide within the fabric wrapped around the annular ring 18.

The sewing cuff 20 may be attached to or otherwise extend around the annular ring 18. The sewing cuff 20 may simply be a layer of fabric or other material covering at least a portion of the annular ring 218. As shown in FIGS. 3A-3D, the sewing cuff 20 may include flexible core material, such as silicone or other elastomeric material, foam, fabric, and the like, which may be attached to or otherwise extend around the annular ring 18, e.g., from an upper edge of the annular ring 18. The core may include a solid wall or a lattice structure, and may be maintained adjacent the annular ring 18 by the surrounding fabric or may be attached to the annular ring 18, e.g., along an upper edge of the annular ring 18. Additional information on materials and methods for making and using the gasket member 12, e.g., the annular ring 18, sewing cuff 20, and/or other components may be found in application Ser. No. 11/069,081, incorporated by reference above.

The collar 22 may be attached to or otherwise extend upwardly from the annular ring 18 and/or the sewing cuff 20. As shown, the collar 22 may include a core 23, which may be separate from the core of the sewing cuff 20. The core 23 and the core of the sewing cuff 20 may be attached to one another, e.g., by bonding fusing, interference fit, and the like, and/or may be maintained adjacent one another by the surrounding fabric. Alternatively, the core 23 of the collar 22 and the core of the sewing cuff 22 may be formed as a unitary piece, e.g., by molding, cutting and/or machining from a blank, and the like. In a further alternative, the collar 22 may be disposed adjacent the sewing cuff 20 and/or annular ring 18, and attached thereto, e.g., using one or more sutures or other connectors (not shown).

Figure 9A:
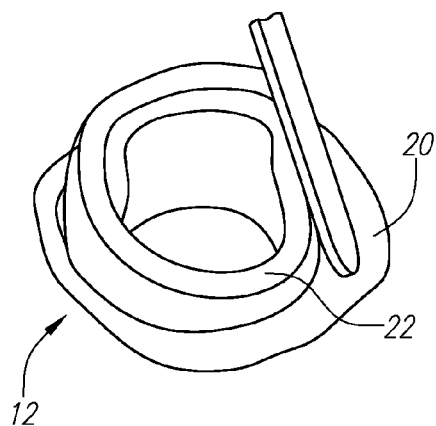
FIGS. 9A and 9B are perspective view of the gasket member of FIGS. 3A-3D, showing flexibility of a collar of the gasket member allowing the collar to be compressed or diverted to provide access to a sewing ring of the gasket member.
Figure 9B:
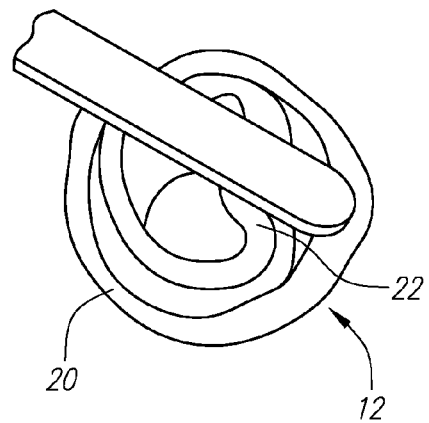
Figure 10:
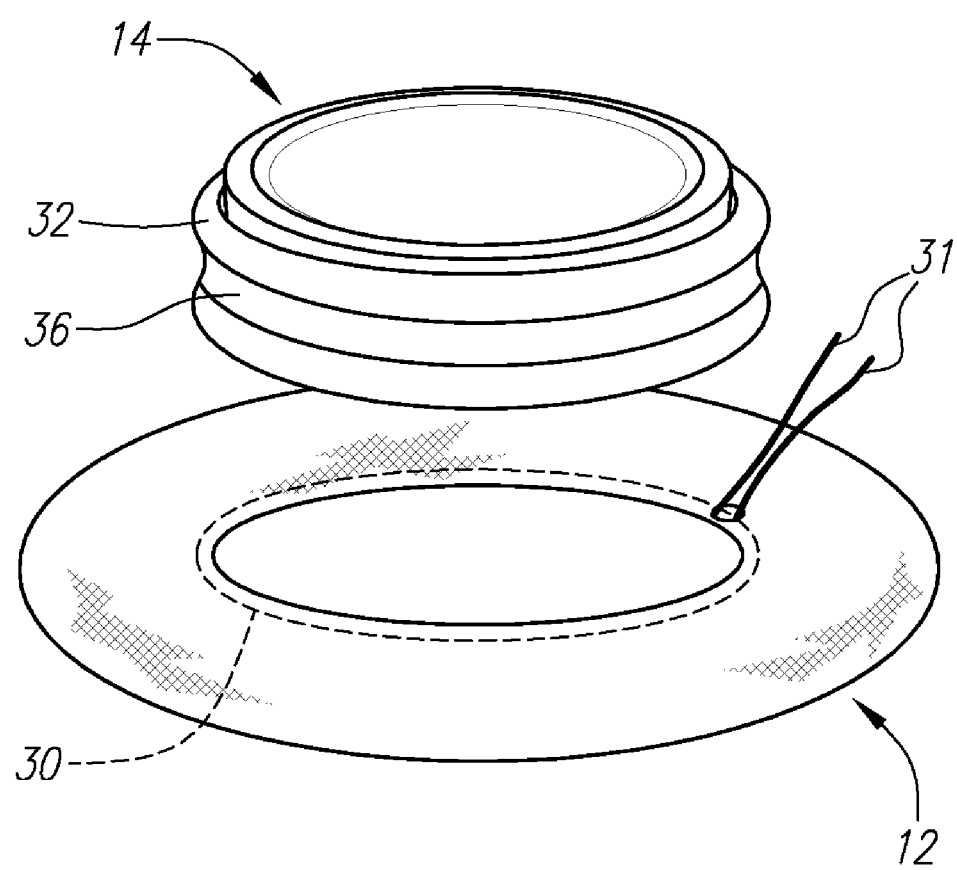
FIG. 10 is a perspective view of a mechanical valve including a frame disposed adjacent a portion of a collar, showing a groove in the frame that may engage with the collar when a drawstring on the collar is tightened.

The material of the core 23 may be substantially flexible, e.g., manufactured in a desired annular shape, yet easily deformed, e.g., deflected, stretched, and/or compressed, as demonstrated in FIGS. 9A and 9B. Exemplary materials for the core include silicone or other elastomeric materials, foam, fabric, felt, polymers, and the like, e.g. similar to the sewing cuff 20. The materials may be molded or otherwise formed into the core, e.g., using known molding, extrusion, cutting, machining, or other manufacturing procedures.

In the embodiment shown in FIGS. 6A-6D, the core 23 may be formed from a cylindrical or tubular section of material, e.g., silicone, which may have portions cut away or otherwise removed to provide the final shape and/or features of the core 23. Alternatively, the core 23 may be molded or otherwise formed to include its final shape and/or features. The core 23 may have a substantially uniform inner and/or outer diameter, or, alternatively, the core 23 may be tapered, e.g., such that a lower edge of the core 23 is narrower than an upper edge, as described further below.

Figure 7A:
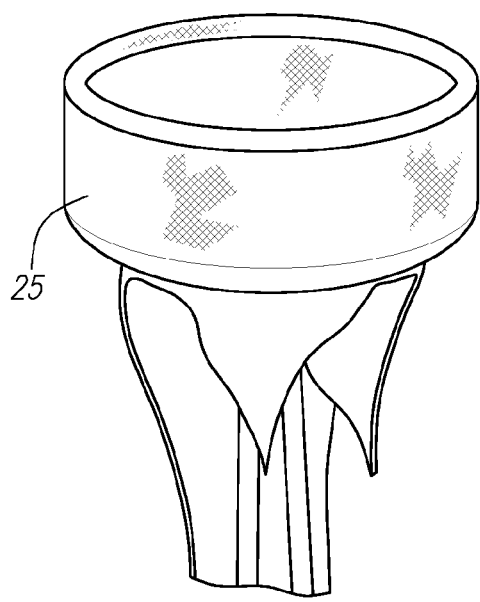
FIGS. 7A-7C show a method for covering the core of FIGS. 6A-6D with fabric to provide a collar for a gasket member.
Figure 7B:
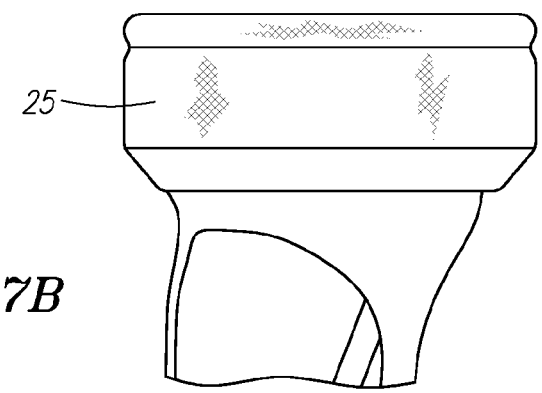
Figure 7C:
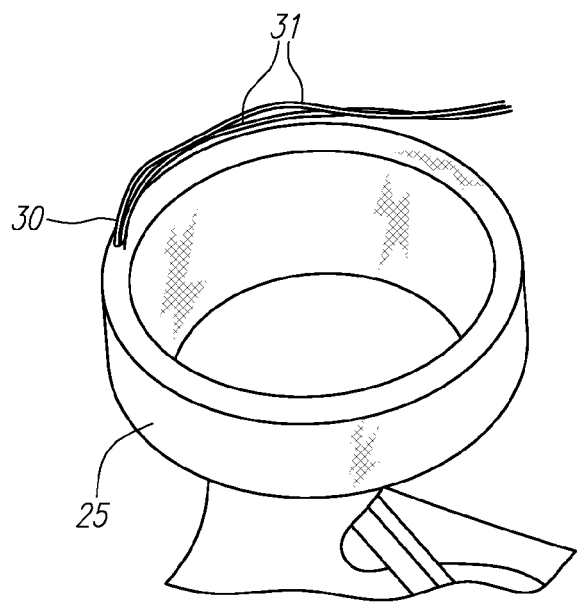

As shown in FIGS. 7A-7C, the core 23 may be covered with fabric 25. Optionally, one or more connectors may be attached to or otherwise provided on the core 23. For example, as shown in FIG. 7C, a drawstring 30 has been provided that at least partially surrounds the core 23. The drawstring 30 may include one or more threads or other filaments that extend around the circumference of the core 23. The fabric 25 may be wrapped around the core 23 such that the fabric 25 also covers the filament of the drawstring 30. Ends 31 of the drawstring 30 may extend through opening in the fabric 25, thereby allowing the ends 31 to be pulled by a user, e.g., to constrict and/or compress the core 23 radially inwardly. Alternatively, other connectors (not shown) may be provided on the collar 22 that may interlock or otherwise engage mating connectors or other features on the valve member 14, e.g., such as those disclosed in application Ser. No. 60/748,639, filed Dec. 7, 2005, Ser. No. 11/279,246, filed Apr. 10, 2006, and 60/746,038, filed Apr. 29, 2006, the disclosures of which are expressly incorporated by reference herein, or in the other applications incorporated by reference above.

Figure 3A:
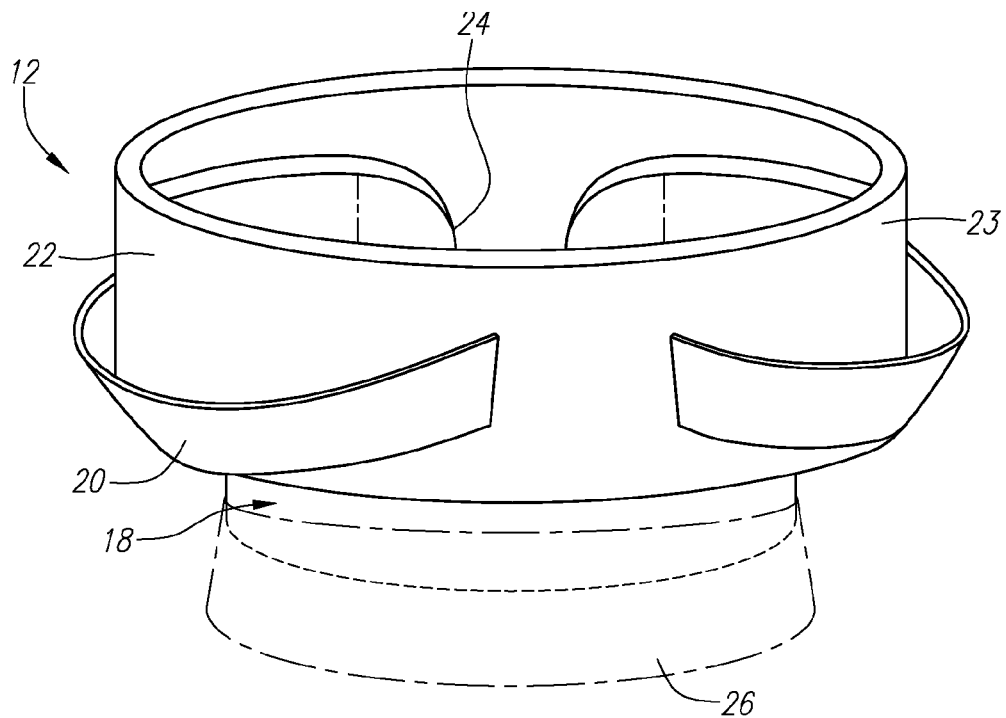
FIGS. 3A and 3B are perspective and top views, respectively, of an exemplary embodiment of a gasket member (with a fabric covering removed for clarity) that may be provided with the heart valve assembly of FIG. 1.
Figure 3B:
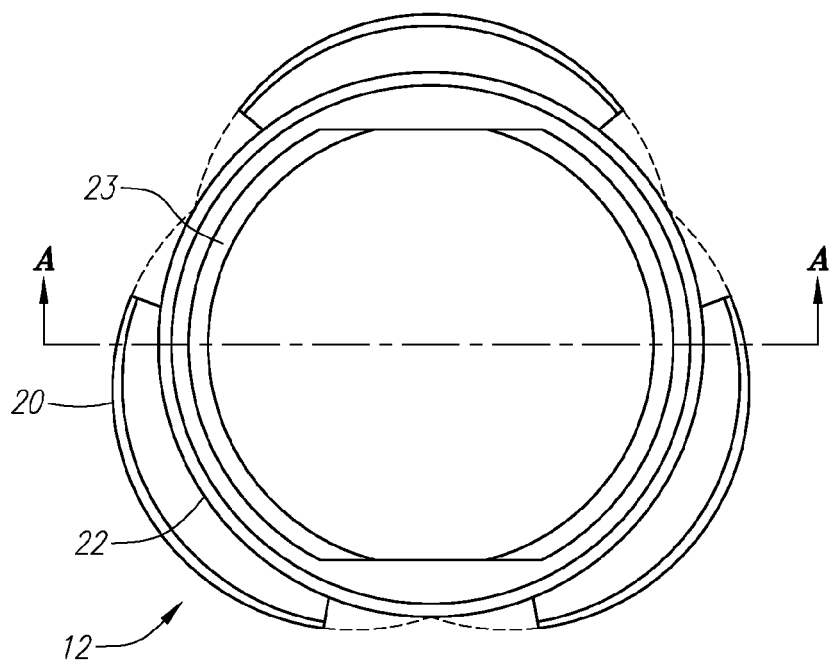
Figure 3C:
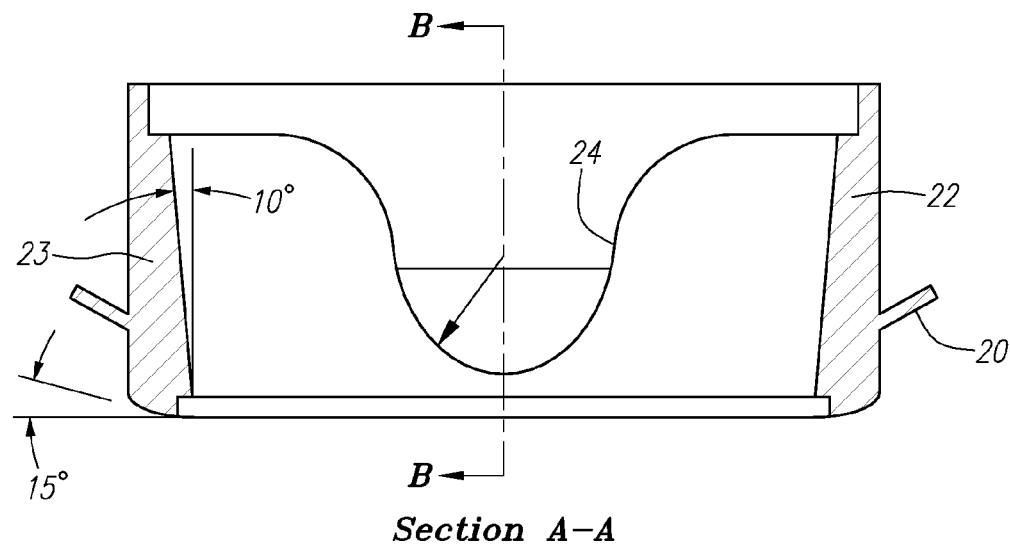
FIG. 3C is a cross-sectional view of the gasket member of FIG. 3B taken along line A-A.
Figure 3D:
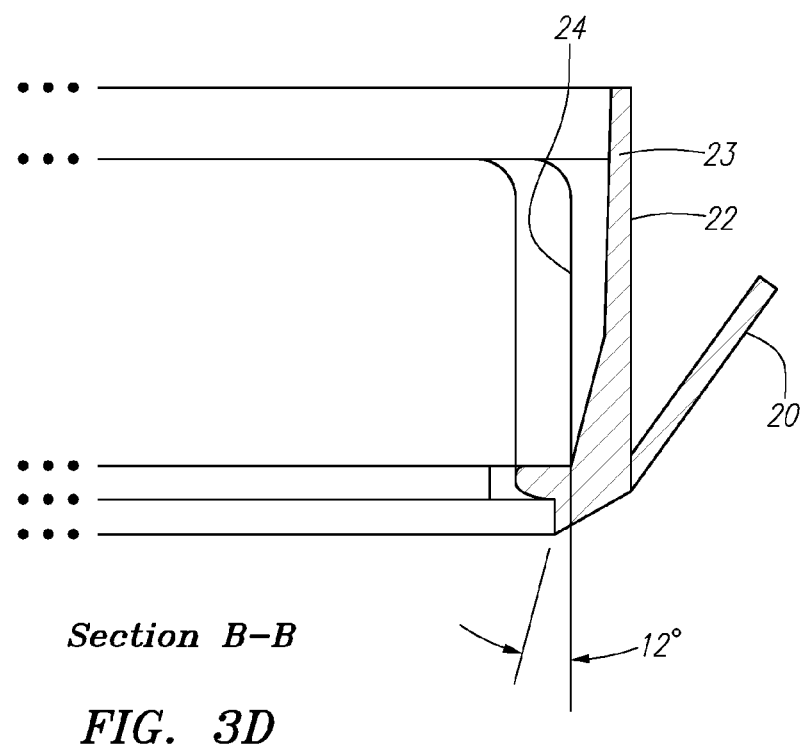
FIG. 3D is a cross-sectional view of the gasket member of FIG. 3C taken along line B-B.
Figure 5:
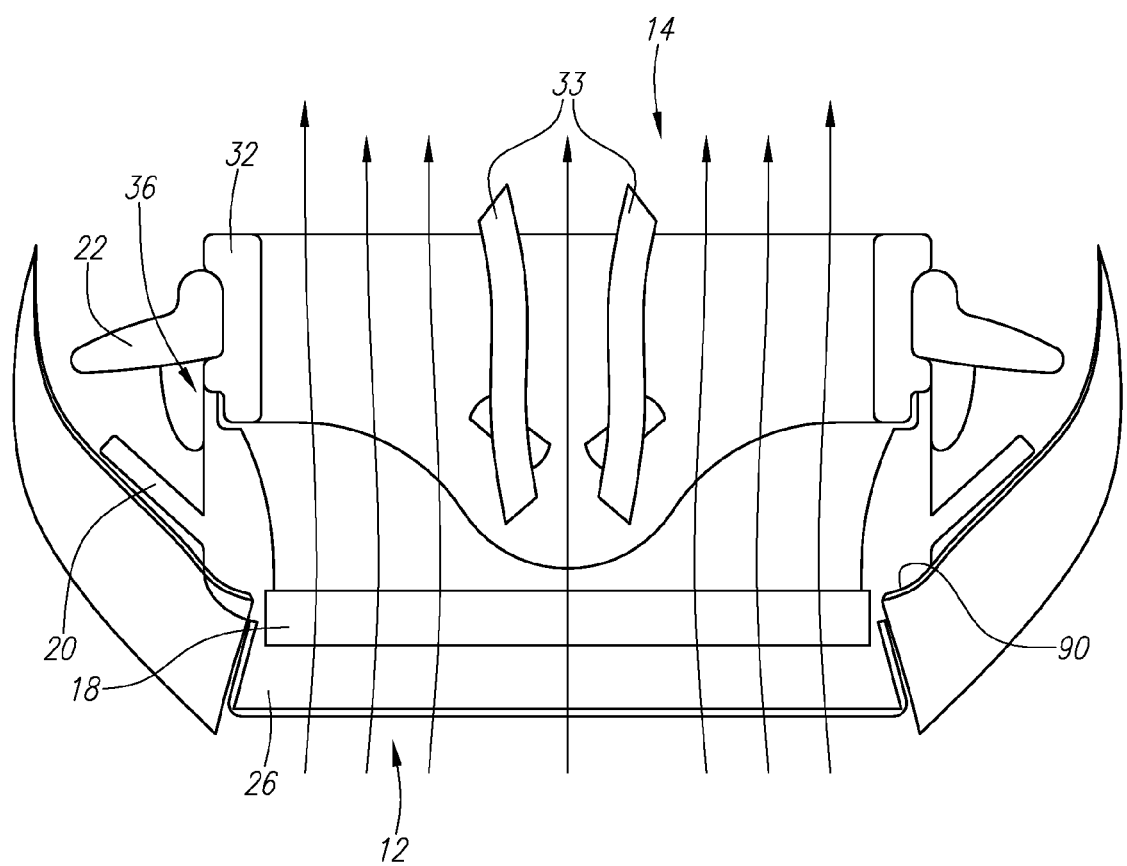
FIG. 5 is a cross-sectional view showing the heart valve assembly of FIGS. 4A and 4B implanted within a tissue annulus of a patient.
Figure 6A:
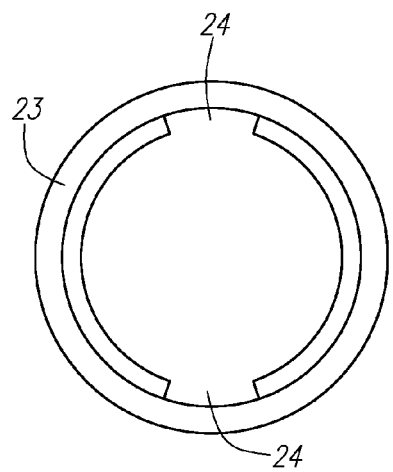
FIGS. 6A-6D are top, two perspective, and side views, respectively, of a core for a collar that may be included in a gasket member.
Figure 6B:
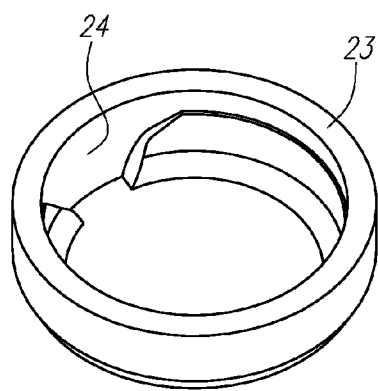
Figure 6C:
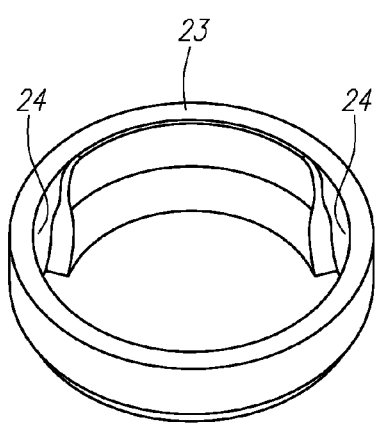
Figure 6D:
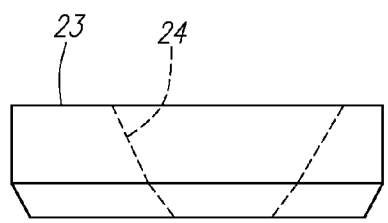

As best seen in FIG. 3C, the collar 22 may include one or more grooves or pockets 24 formed within the collar 22. For example, the collar 22 may include a pair of opposing grooves on an inner surface thereof, which may accommodate the ears 34 of the valve member 14 shown in FIG. 2. The collar 22 may have sufficient height to accommodate receiving the frame 32 of the valve member 14 without the ears 34 extending down into the annular ring 18, e.g., as can be seen in FIG. 5, which may otherwise at least partially obstruct the passage through a biological annulus. The collar 22 may have sufficient structural integrity to support the valve member 14, yet be sufficiently flexible to be deformable to facilitate introduction into a patient's body and/or to move the collar 22 away to accommodate delivery of one or more connectors into the sewing cuff 20, as described elsewhere herein.

During use, the gasket member 12 may be implanted within a patient's body, e.g., within or adjacent to a biological annulus 90, as shown in FIG. 5, similar to the methods disclosed in the applications incorporated by reference above. The biological annulus 90 may be the site for replacement of an existing natural or previously implanted prosthetic valve, such as a tricuspid, mitral, aortic, or pulmonary valve within a patient's heart (not shown). The biological annulus may extend from a supra annular region, e.g., the Sinus of Valsalva for an aortic valve, through a native valve site, e.g., a site where the aortic valve has been removed, to a sub-annular region.

With the annular ring 18 contracted into a relatively small diameter (if the annular ring 18 is radially compressible), the gasket member 12 may be advanced into the annulus 90 using a delivery tool (not shown). The gasket member 12 may be advanced until the annular ring 18 extends at least partially into the biological annulus 90. In one embodiment, the annular ring 18 may extend entirely through the biological annulus 90, with the lower edge of the annular ring 18 remaining free within the sub-annular space below the biological annulus 90. Optionally, as shown in FIGS. 4B and 5, the gasket member 12 may include a flexible skirt 26 that extends through the annulus 90. The skirt 26 may be biased to extend outwardly as shown to provide a smooth transition and/or enhance a seal between the heart vale assembly 10 and the biological annulus 90.

If the annular ring 18 is expandable or otherwise compressed, the annular ring 18 may then be expanded within the biological annulus 90, e.g., to dilate the biological annulus 90 or otherwise direct the surrounding tissue outwardly against the underlying tissue structures. For example, the annular ring 218 may simply be released by the delivery tool, whereupon the annular ring 18 may resiliently expand against the tissue surrounding the biological annulus 90, thereby substantially securing the annular ring 18 (and consequently, the gasket member 12) relative to the biological annulus 90. In addition or alternatively, a dilation tool (not shown) may be advanced into the gasket member 12 and expanded to forcibly (e.g., plastically) expand the annular ring 18 within the biological annulus 90.

If the sewing cuff 20 is restrained by the delivery tool, the sewing cuff 20 may be released to allow the sewing cuff 20 to contact the surrounding tissue, e.g., within the aortic root above the biological annulus 90. The sewing cuff 20 may contact the tissue within the supra-annular space above the biological annulus 90, as shown in FIG. 5, although the sewing cuff 20 may not provide any structural support of the annular ring 18. Because of the floppy (i.e., flexible and conformable) nature of the core of the sewing cuff 20, the sewing cuff 20 may adopt the shape of the surrounding tissue, e.g., lying flatter within the coronary sinus regions, while becoming more vertical adjacent the commissures, as explained in the applications incorporated by reference above.

With the gasket member 12 in place, a plurality of fasteners, e.g., clips, staples, sutures, and the like (not shown), may be directed through the sewing cuff 20 into the tissue surrounding the biological annulus to secure the gasket member 12 relative to the biological annulus. If necessary to facilitate access to the sewing cuff 20, local portions of the collar 22 may be at least partially deflected out of the way, as shown in FIGS. 9A and 9B. The collar 22 may be sufficiently resilient to return to its annular shape upon release. Additional information on fasteners and apparatus and methods for delivering them may be found in application Ser. No. 10/681,700, filed Oct. 8, 2003 and Ser. No. 11/004,445, filed Dec. 3, 2004, the entire disclosures of which are expressly incorporated by reference herein.

Figure 8A:
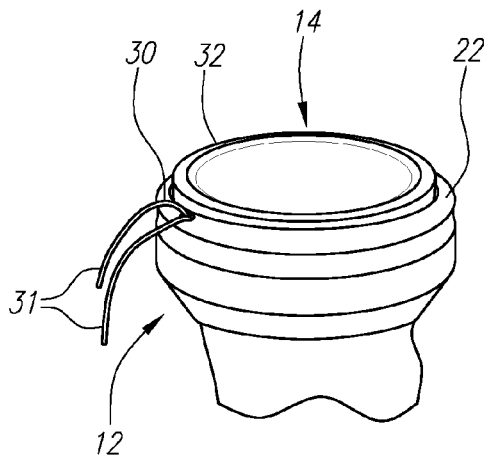
FIG. 8A is a perspective view of a mechanical valve secured to the collar of FIG. 7C by a drawstring.
Figure 8B:
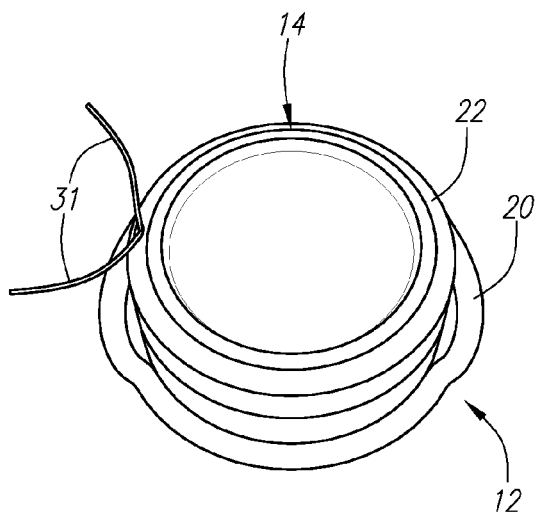
FIG. 8B is a perspective view of the mechanical valve of FIG. 8A being secured to a completed gasket member by a drawstring.

The valve member 14 may then be advanced into the biological annulus, e.g. using another delivery tool or the same tool (not shown) used to deliver the gasket member 12. The valve member 14 may then be secured to the collar 22, e.g., using one or more connectors. For example, as described above, in one embodiment, the collar 22 may include a drawstring 30, as shown in FIG. 7C. After inserting the valve member 14 at least partially into the collar 22, as shown in FIGS. 8A and 8B, the ends 31 may be pulled to tighten the drawstring 30 around the frame 32 of the valve member 14 to secure the valve member 14 relative to the collar 22. Optionally, the frame 32 may include an annular groove 36 or other feature(s) (not shown) that may receive a portion of the collar 22 or otherwise engage the collar when the drawstring 30 is tightened.

Alternatively, one or more sutures 40 may be directed through a sewing cuff 39 on the valve member 14 and the fabric and/or core of the collar 22, e.g., as shown in FIG. 1. In a further alternative, the valve member 14 and/or collar 22 may include cooperating clips, detents, and the like (not shown) that may self-engage when the valve member 14 is docked into the collar 22, similar to the embodiments described in the applications incorporated by reference above. In still another alternative, the gasket member 12 may include a plurality of leaders or other elongate guides (not shown), which may be directed through a sewing cuff 39 or other portion of the valve member 14, similar to the apparatus and methods disclosed in application Ser. No. 60/748,639 and 60/746,038, incorporated by reference above. For example, the leaders may be sutures, and knots may be directed down the sutures to secure the valve member 14 to the collar 22, whereupon the sutures may be cut or otherwise severed. Alternatively, other guide members (not shown) may be provided that may be directed through the sewing cuff 39, e.g., through receivers or other mating connectors (also not shown) in the sewing cuff 22 or simply by "picking up" strands of the fabric of the sewing cuff 22, as described in the applications incorporated by reference above.

Once the valve member 14 is secured, any tools may be removed, and the procedure completed using known methods.

In an alternative embodiment, the valve member 14 may be secured to the collar 22 (or otherwise to the gasket member 12, as described elsewhere herein) before introduction into the patient's body. For example, immediately before implantation, a user may select a desired size valve member 14 and direct the valve member into engagement with the collar 22, e.g., using one or more cooperating detents or other connectors as described herein or in the applications incorporated by reference above. In a further alternative, the valve member 14 may be secured to the collar 22 during manufacturing, and shipped pre-assembled as a single piece.

The resulting heart valve assembly 10 may be introduced into a tissue annulus, e.g., a site of a native or previously implanted prosthetic valve (not shown), as a single component. For example, a plurality of sutures may be placed in tissue surrounding the tissue annulus, e.g., using conventional needle and suture devices. The sutures may be directed through a portion of the heart valve assembly 10, e.g., through the sewing cuff 20, valve frame, or other portion of the heart valve assembly 10. In one embodiment, a needle on one end of each suture may be directed through fabric on the heart valve assembly, i.e., to pick up one or more strands of the fabric.

Once several sutures have been directed through the heart valve assembly 10, e.g., spaced apart around the circumference of the heart valve assembly 10, the heart valve assembly 10 may be advanced or "parachuted" down the sutures into the tissue annulus. Knots may be tied in the sutures to secure the heart valve assembly 10 within or otherwise to the tissue annulus. Excess suture material may then be cut off or otherwise severed. Optionally, other connectors, e.g., staples, clips, and the like, may be delivered through the sewing cuff 20 and/or other portion of the heart valve assembly 10 into the surrounding tissue, in addition to or instead of the sutures. Thus, the heart valve assembly 10 may be delivered more analogously to a one-piece valve.

One advantage of the apparatus and methods described herein is that a valve member 14 may be selected that is larger than conventional one-piece valves. Because the valve member 14 is secured to or otherwise supported by the collar 22, the valve member 14 may be disposed above the tissue annulus, e.g., within the sinus of Valsalva, upon implantation within the aortic valve annulus. Because this space is larger than the tissue annulus, a relatively larger valve member 14 may be selected than if the valve member 14 were disposed within the aortic valve annulus.

The collar 22 may provide a substantially smooth and/or continuous transition from the valve member 14 into the tissue annulus, thereby providing improved flow through the heart valve assembly 10 and/or tissue annulus after implantation. Thus, an inner surface of the collar 22 may be designed to transition substantially smoothly from a larger upper edge, corresponding to the size of the valve member 14 down to a lower edge corresponding to the size of the annular member 18 extending through the biological annulus. This may enhance hemodynamics of blood flowing through the biological annulus, as compared to conventional valves.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A heart valve assembly, comprising:
   an annular prosthesis implantable within a natural valve annulus, the annular prosthesis comprising an annular member configured to be received in a biological annulus, a sewing cuff extending radially outwardly from the annular member, and a collar extending upwardly from the annular member; and
   a prosthetic valve comprising a frame securable to the collar, wherein the frame includes a first ear and a second ear, wherein the first and second ears extend downwardly from the frame,
   wherein the collar includes a first pocket configured to receive the first ear and a second pocket configured to receive the second ear, and
   wherein the collar defines an interior lumen having a longitudinal axis, wherein the collar includes an internal wall and an external wall, wherein the internal wall is closer to the longitudinal axis than the external wall, and wherein the first and second pockets are formed in the internal wall of the collar.

2. The heart valve assembly of claim 1, further comprising one or more connectors for securing the prosthetic valve to the annular prosthesis.

3. The heart valve assembly of claim 2, wherein the one or more connectors comprises a drawstring on the collar.

4. The heart valve assembly of claim 1, wherein the prosthetic valve comprises a mechanical valve.

5. The heart valve assembly of claim 1, wherein the prosthetic valve comprises a bioprosthetic valve.

6. The heart valve assembly of claim 1, wherein the first and second pockets are open to the interior lumen.

7. A method for implanting a prosthetic heart valve assembly to replace a natural or prosthetic heart valve implanted within a biological annulus below a sinus cavity, the method comprising:
   obtaining a gasket member comprising an annular ring sized for delivery into the biological annulus, the gasket member comprising an annular transition extending upwardly from the annular ring, wherein the annular transition comprises a first pocket and a second pocket, wherein the annular transition defines an interior lumen having a longitudinal axis, wherein the annular transition includes an internal wall and an external wall, wherein the internal wall is closer to the longitudinal axis than the external wall, arid wherein the first and second lockets are formed in the internal wall of the annular transition;
   obtaining a valve member that has a cross-section larger than the annular ring, wherein the valve member comprises a frame including first and second ears extending downwardly from the frame, and wherein the first ear is configured to mate with the first pocket and the second ear is configured to mate with the second pocket to secure the valve member to the frame;
   connecting the valve member to the annular transition to provide a heart valve assembly;
   introducing the heart valve assembly towards the biological annulus such that the annular ring is disposed within the biological annulus and the valve member is disposed within the sinus cavity; and
   securing the heart valve assembly to tissue adjacent the biological annulus.

8. The method of claim 7, wherein the first and second pockets are open to the interior lumen.

9. A method for implanting a prosthetic heart valve assembly within a biological annulus, comprising:
   obtaining a heart valve assembly comprising an annular member sized for delivery into the biological annulus, an annular transition extending upwardly from the annular ring, and a valve member secured to the annular transition that has a cross-section larger than the annular member, wherein the valve member comprises a frame including first and second ears extending downwardly from the frame, wherein the annular transition includes a first pocket configured to receive the first ear and a second pocket configured to receive the second ear, wherein the annular transition defines an interior lumen having a longitudinal axis, wherein the annular transition includes an internal wall and an external wall, wherein the internal wall is closer to the longitudinal axis than the external wall, and wherein the first and second pockets are formed in the internal wall of the annular transition;
   introducing the heart valve assembly towards the biological annulus such that the annular member is disposed within the biological annulus and the valve member is disposed above the biological annulus; and
   securing the heart valve assembly to tissue adjacent the biological annulus.

10. The method of claim 9, wherein introducing the heart valve assembly comprises:
    placing a plurality of sutures through tissue surrounding the biological annulus;
    directing the sutures through portions of the heart valve assembly; and
    advancing the heart valve assembly down the sutures until the annular member is disposed within the biological annulus.

11. The method of claim 10, wherein the heart valve assembly is secured to tissue adjacent the biological annulus by tying knots in the sutures.

12. The method of claim 9, wherein the annular transition comprises a collar including an upper edge to which the valve member is secured, the annular transition providing a transition inwardly from the upper edge towards the annular member for facilitating flow through the heart valve assembly.

13. The method of claim 9, further comprising selecting a valve member having a predetermined size corresponding to a sinus cavity above the biological annulus, and securing the selected valve member to the annular transition.

14. The method of claim 9, wherein the first and second pockets are open to the interior lumen.

\* \* \* \* \*